United States Patent
Fromme et al.

(10) Patent No.: US 12,215,094 B2
(45) Date of Patent: Feb. 4, 2025

(54) SOLID FORMS OF 2-METHYL-1-[(4-[6-(TRIFLUOROMETHYL) PYRIDIN-2-YL]-6-{[2-(TRIFLUOROMETHYL) PYRIDIN-4-YL]AMINO}-1,3,5-TRIAZIN-2-YL) AMINO]PROPAN-2-OL

(71) Applicant: Celgene Corporation, Summit, NJ (US)

(72) Inventors: Eric A. Fromme, Flemington, NJ (US); Kevin J. Klopfer, Flemington, NJ (US)

(73) Assignee: Celgene Corporation, Summit, NJ (US)

( * ) Notice: Subject to any disclaimer, the term of this patent is extended or adjusted under 35 U.S.C. 154(b) by 812 days.

(21) Appl. No.: 17/290,240

(22) PCT Filed: Nov. 1, 2019

(86) PCT No.: PCT/US2019/059379
§ 371 (c)(1),
(2) Date: Apr. 30, 2021

(87) PCT Pub. No.: WO2020/092894
PCT Pub. Date: May 7, 2020

(65) Prior Publication Data
US 2021/0403452 A1 Dec. 30, 2021

Related U.S. Application Data

(60) Provisional application No. 62/755,263, filed on Nov. 2, 2018.

(51) Int. Cl.
*C07D 401/14* (2006.01)
*A61K 45/06* (2006.01)

(52) U.S. Cl.
CPC ............ *C07D 401/14* (2013.01); *A61K 45/06* (2013.01); *C07B 2200/13* (2013.01)

(58) Field of Classification Search
CPC .. C07D 401/14; A61K 45/06; C07B 2200/13; A61P 35/00
See application file for complete search history.

(56) References Cited

U.S. PATENT DOCUMENTS

| | | |
|---|---|---|
| 9,512,107 B2 | 12/2016 | Cianchetta et al. |
| 9,656,999 B2 | 5/2017 | Cianchetta et al. |
| 9,694,013 B2 | 7/2017 | Agresta |
| 9,724,350 B2 | 8/2017 | Travins et al. |

(Continued)

FOREIGN PATENT DOCUMENTS

| | | | |
|---|---|---|---|
| WO | WO 2015/018060 | 2/2015 | |
| WO | WO-2015017821 A2 * | 2/2015 | ........... A61K 31/444 |
| WO | WO 2018/048847 A1 | 3/2018 | |

OTHER PUBLICATIONS

Yang et al. IDH1 and IDH2 mutations in tumorigenesis: mechanistic insights and clinical perspectives. Clin Cancer Res. 2012; 18(20):5562-5571. (Year: 2012).*

(Continued)

*Primary Examiner* — Matthew P Coughlin
*Assistant Examiner* — Ashli Ariana Chicks
(74) *Attorney, Agent, or Firm* — Jones Day

(57) ABSTRACT

Solid forms comprising 2-methyl-1-[(4-[6-(trifluoromethyl) pyridin-2-yl]-6-{[2-(trifluoromethyl)pyridin-4-yl] amino-1, 3,5-triazin-2-yl)amino]propan-2-ol, compositions comprising the solid forms, methods of making the solid forms and methods of using the solid forms are disclosed.

23 Claims, 10 Drawing Sheets

(56) References Cited

U.S. PATENT DOCUMENTS

| | | | |
|---|---|---|---|
| 9,732,062 B2 | 8/2017 | Cianchetta et al. | |
| 9,738,625 B2 | 8/2017 | Agresta et al. | |
| 9,751,863 B2 | 9/2017 | Zhang | |
| 9,889,137 B2 | 2/2018 | Agresta | |
| 10,093,654 B2 | 10/2018 | Agresta et al. | |
| 10,137,130 B2 | 11/2018 | Amatangelo et al. | |
| 10,188,656 B2 | 1/2019 | Wu et al. | |
| 10,201,543 B2 | 2/2019 | Kluge | |
| 10,294,215 B2 | 5/2019 | Cianchetta et al. | |
| 10,434,105 B2 | 10/2019 | Kluge et al. | |
| 10,695,352 B2 | 6/2020 | Chopra et al. | |
| 10,730,854 B2 | 8/2020 | Agresta et al. | |
| 10,905,692 B2 | 2/2021 | Agresta | |
| 11,229,653 B2 | 1/2022 | Levine et al. | |
| 2003/0104062 A1 | 6/2003 | Berner et al. | |
| 2018/0042930 A1 | 2/2018 | Amatangelo et al. | |
| 2018/0064715 A1 | 3/2018 | Bhat et al. | |
| 2022/0017489 A1 | 1/2022 | Fromme et al. | |
| 2022/0017490 A1* | 1/2022 | Fromme | A61K 45/06 |

OTHER PUBLICATIONS

Bayat Mokhtari et al. Combination therapy in combating cancer. Oncotarget. 2017;8(23):38022-38043. (Year: 2017).*

Nussbaumer et al. Analysis of anticancer drugs: A review. Talanta., 85 (2011), pp. 2265-2289. (Year: 2011).*

Hoell et al. End-of-life care in children with hematologic malignancies. Oncotarget. 2017;8(52): 89939-89948. (Year: 2017).*

International Search Report issued on International Appln. No. PCT/US2019/059379, dated Mar. 17, 2020.

* cited by examiner

SOLID FORMS OF 2-METHYL-1-[(4-[6-(TRIFLUOROMETHYL) PYRIDIN-2-YL]-6-{[2-(TRIFLUOROMETHYL) PYRIDIN-4-YL]AMINO}-1,3,5-TRIAZIN-2-YL) AMINO]PROPAN-2-OL

1. RELATED APPLICATIONS

This application is a U.S. National Stage filing under 35 U.S.C. § 371 of International Application No. PCT/US2019/059379, filed Nov. 1, 2019, which claims the benefit of U.S. Provisional Application No. 62/755,263, filed Nov. 2, 2018, the disclosure of each of which is incorporated herein by reference in its entirety.

2. FIELD

Provided herein are solid forms comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, pharmaceutical compositions thereof, and methods of their uses for the treatment of diseases or disorders.

3. BACKGROUND OF THE DISCLOSURE

A primary concern for the manufacture of large-scale pharmaceutical compositions is that the active ingredient should have a stable crystalline morphology to ensure consistent processing parameters and pharmaceutical quality. The active ingredient should possess acceptable properties with respect to hygroscopicity, solubility, and stability, which can be consistently reproduced despite the impact of various environmental conditions such as temperature and humidity. If an unstable crystalline form is used, crystal morphology may change during manufacture and/or storage resulting in quality control problems, and formulation irregularities. Such a change may affect the reproducibility of the manufacturing process and thus lead to pharmaceutical formulations that do not meet the high quality and stringent requirements imposed on formulations of pharmaceutical compositions.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

The polymorphic behavior of pharmaceutically active substances is of great importance in pharmacy and pharmacology. The differences in physical properties exhibited by polymorphs affect practical parameters such as storage stability, compressibility and density (important in pharmaceutical composition manufacturing), and dissolution rates (an important factor in determining bio-availability of an active ingredient). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to thermodynamically more stable polymorph) or both (e.g., tablets of one polymorph are more susceptible to breakdown at high humidity than another polymorph). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While pharmaceutical formulations having improved chemical and physical properties are desired, there is no predictable means for preparing new crystalline forms (e.g., polymorphs) of existing molecules for such formulations. There is a need for crystalline forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol that may possess consistent physical properties over the range of environments that may be encountered during pharmaceutical formulation manufacturing and storage.

SUMMARY OF INVENTION

Provided herein are solid forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In one embodiment, the solid form is crystalline Form G of 2-methyl-1-[(4-[6-(trifluoromethyl)pyridin-2-yl]-6-{[2-(trifluoromethyl)pyridin-4-yl]amino}-1,3,5-triazin-2-yl) amino]propan-2-ol. In another embodiment, the solid form is crystalline Form H of 2-methyl-1-[(4-[6-(trifluoromethyl) pyridin-2-yl]-6-{[2-(trifluoromethyl)pyridin-4-yl]amino}-1,3,5-triazin-2-yl)amino]propan-2-ol. In yet another embodiment, the solid form is crystalline Form J of 2-methyl-1-[(4-[6-(trifluoromethyl)pyridin-2-yl]-6-{[2-(trifluoromethyl)pyridin-4-yl]amino}-1,3,5-triazin-2-yl) amino]propan-2-ol. In yet another embodiment, the solid form is crystalline Form K of 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol. Without intending to be limited by any particular theory, certain solid forms provided herein have particular advantageous physical and/or chemical properties making them useful, e.g., for manufacturing, processing, formulation and/or storage, while also possessing particularly advantageous biological properties, such as, e.g., bioavailability and/or biological activity.

Also provided herein are methods of preparing the solid forms provided herein.

Also provided herein are pharmaceutical compositions comprising one or more solid forms provided herein.

Also provided herein are methods of treating and managing various diseases or disorders comprising administering to a patient a therapeutically effective amount of a solid form provided herein.

In certain embodiments, provided herein are methods of treating hematological malignancies or solid tumors, each characterized by the presence of a mutant allele of IDH2 comprising administering a solid form provided herein.

In one embodiment, the hematological malignancy is selected from acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL), blastic plasmacytoid dendritic cell neoplasm and myeloproliferative neoplasm (MPN), each characterized by the presence of a mutant allele of IDH2.

In one embodiment, the solid tumor is selected from glioma, melanoma, chondrosarcoma, and cholangiocarcinoma, each characterized by the presence of a mutant allele of IDH2.

In certain embodiments, the solid form provided herein is used for oral administration in patients for treating a proliferative disease, such as cancer, characterized by the presence of a mutant allele of IDH2.

In certain embodiments, the solid form provided herein is used for oral administration in pediatric patients for treating a proliferative disease, such as cancer, characterized by the presence of a mutant allele of IDH2.

DETAILED DESCRIPTION OF THE INVENTION

Figure 1:
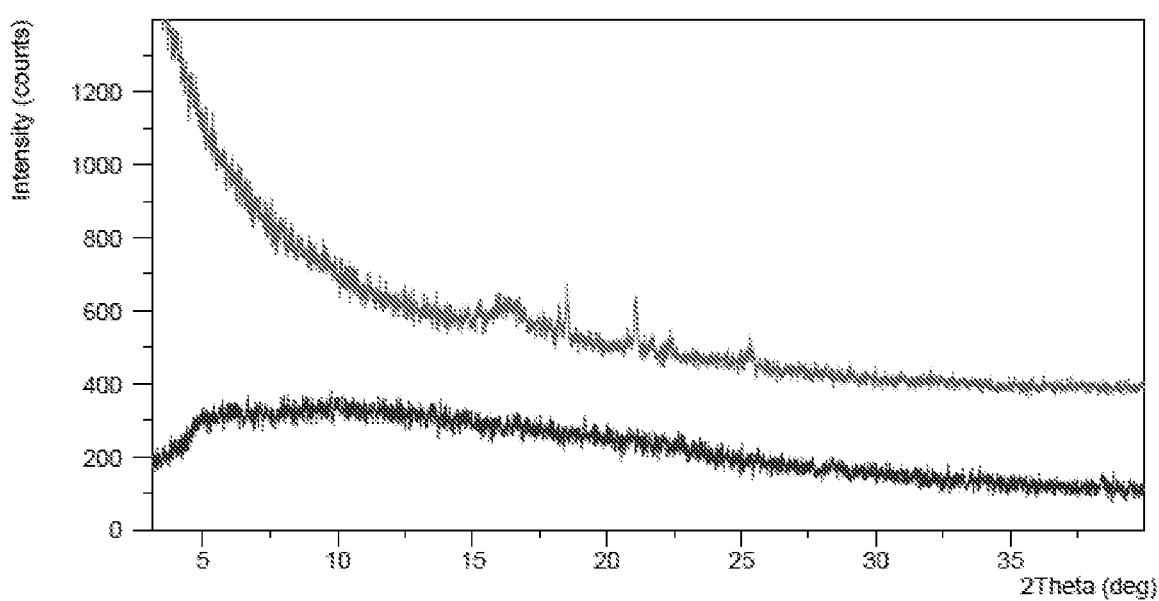
FIG. 1 provides an X-ray powder diffractogram (XRPD) of Form G of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used above, and throughout the description of the invention, the following terms, unless otherwise indicated, shall be understood to have the following meanings.

As used in this application, the singular form "a", "an" and "the" include plural references unless the context clearly dictates otherwise. For example, the term "an intragranular excipient" includes one or more intragranular excipients.

Compound 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate (or mesylate) is also known as enasidenib.

The terms "AG 221" or "AG221" refer to 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, including solid forms thereof, or 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate, including solid forms thereof.

2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is currently marketed in the U.S. by Celgene Corporation, as once-daily oral tablets for the treatment of adult patients with relapsed or refractory acute myeloid leukemia (AML) who have an IDH2 mutation, under the trade name IDHIFA®.

The term "solid form" refers a crystal form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

Unless otherwise specified, the term "crystalline" and related terms used herein, when used to describe a substance, component, product, or form, mean that the substance, component, product, or form is substantially crystalline, for example, as determined by X-ray diffraction. (see, e.g., *Remington's Pharmaceutical Sciences*, 18$^{th}$ ed., Mack Publishing, Easton PA, 173 (1990); *The United States Pharmacopeia*, 23$^{rd}$ ed., 1843-1844 (1995)).

Unless otherwise specified, the term "crystal form," "crystal forms," and related terms herein refer to crystalline modifications comprising a given substance. In some embodiments, a crystal form of a substance may be substantially free of amorphous forms and/or other crystal forms. In other embodiments, a crystal form of a substance may contain less than about 1%, 2%, 3%, 4%, 5%, 10%, 15%, 20%, 25%, 30%, 35%, 40%, 45%, or 50% of one or more amorphous form(s) and/or other crystal form(s) on a weight basis. Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to a crystal or a mixture of crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

A "pharmaceutically acceptable excipient, diluent or carrier," refers to a substance that aids the administration of an active agent to a subject by, for example, modifying the stability of an active agent or modifying the absorption by a subject upon administration. A pharmaceutically acceptable excipient typically has no significant adverse toxicological effect on the patient. Examples of pharmaceutically acceptable excipients include, for example bulking agents, buffers, binders, fillers, disintegrants, lubricants, coatings, sweeteners, flavors, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., 6$^{th}$ Ed., The Pharmaceutical Press, RPS Publishing (2009). The terms "bulking agent", and "buffer" are used in accordance with the plain and ordinary meaning within the art.

The term "treat" means decrease, attenuate, diminish, or stabilize the development or progression of a disease/disorder (e.g., a cancer such as AMVL, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma), or lessen the severity of the disease/disorder (e.g., a cancer such as AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma), or improve the symptoms associated with the disease/disorder (e.g., AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma), each characterized by the presence of a mutant allele of IDH2.

As used herein, and unless otherwise indicated, the terms "manage," "managing" and "management" encompass preventing the recurrence of the specified disease or disorder in a patient who has already suffered from the disease or disorder, or lengthening the time that a patient who has suffered from the disease or disorder remains in remission. The terms encompass modulating the threshold, development or duration of the disease or disorder, or changing the way that a patient responds to the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, that provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, "administer" or "administration" refers to the act of physically delivering a substance as it exists outside the body into a subject. Administration includes all forms known in the art for delivering therapeutic agents, including but not limited to oral, topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal).

The term "co-administer" as used herein with respect to an additional cancer therapeutic agents means that the additional cancer therapeutic agent may be administered prior to, consecutively with, or following the administration of a composition provided herein. In such combination therapy treatment, the second therapeutic agent(s) is administered by conventional methods.

The terms "subject" and "patient," are herein used interchangeably and refer to a living organism suffering from one or more of the diseases described herein (e.g., AML) that can be treated by administration of a composition described herein. Non-limiting examples of organisms include humans, other mammals, bovines, rats, mice, dogs, monkeys, goat, sheep, cows, deer, and other non-mammalian animals. In certain embodiments, a subject is human. A human subject can be between the ages of about 1 year old to about 100 years old. In certain embodiments, subjects herein can be characterized by the disease being treated (e.g., a "AML subject", a "cancer subject", or a "leukemia subject").

As used herein, the term "pediatric patient" refers to a patient 21 years or younger, in certain embodiments, a patient 18 years or younger, in certain embodiments, a patient 16 years or younger, in certain embodiments, a patient 14 years or younger, in certain embodiments, a patient 12 years or younger, in certain embodiments, a patient 10 years or younger, or in certain embodiments, a patient 8 years or younger.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2° 2θ while still describing the particular XRPD peak.

Unless otherwise specified, to the extent that there is a discrepancy between a depicted chemical structure of a compound provided herein and a chemical name of a compound provided herein, the chemical structure shall control.

Compound

In certain embodiments, provided herein are solid forms comprising 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol having the following formula:

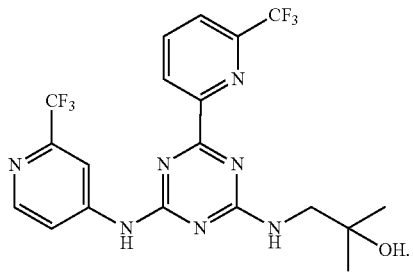 [SMILES: CC(C)(O)CNc1nc(Nc2ccnc(C(F)(F)F)c2)nc(-c2cccc(C(F)(F)F)n2)n1]

In one embodiment, 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol can be synthesized using methods described in U.S. Pat. Nos. 9,512,107; 9,656,999; 9,732,062; 9,738,625; 9,751,863 and U.S. Publication No. 2017/0305885 A1, and PCT Publication No. WO 2016/126798, all of which are incorporated herein in their entireties.

Certain polymorphic forms of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, including Form 1, Form 2, Form 17 and Form 19, are described in U.S. Pat. No. 9,738,625 and WO 2016/126798, the entirety of each of which is incorporated herein by reference.

Crystalline Forms

Form G

In one embodiment, a single crystalline form, Form G, of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is characterized by the X-ray powder diffraction (XRPD) pattern shown in FIG. 1, and data shown in Table 1, obtained using CuKα radiation. In a particular embodiment, the polymorph can be characterized by one or more of the peaks taken from FIG. 1, as shown in Table 1. In one embodiment, the polymorph can be characterized by an X-ray powder diffraction pattern comprising peaks at about 18.52 and 21.09° 2θ. In one embodiment, the polymorph can be characterized by an X-ray powder diffraction pattern comprising peaks at about 18.52, 21.09, 22.40 and 25.36° 2θ. In one embodiment, the polymorph can be characterized by an X-ray powder diffraction pattern comprising one or two or three or four or five or more of the peaks shown in Table 1.

TABLE 1

| Peak List for Form G | |
|---|---|
| Angle (° 2θ) | Relative Intensity |
| 9.630517 | 16.55 |
| 16.328970 | 14.94 |
| 18.520670 | 54.83 |
| 21.085520 | 100.00 |
| 22.400460 | 39.80 |
| 25.359040 | 43.08 |

Figure 2:
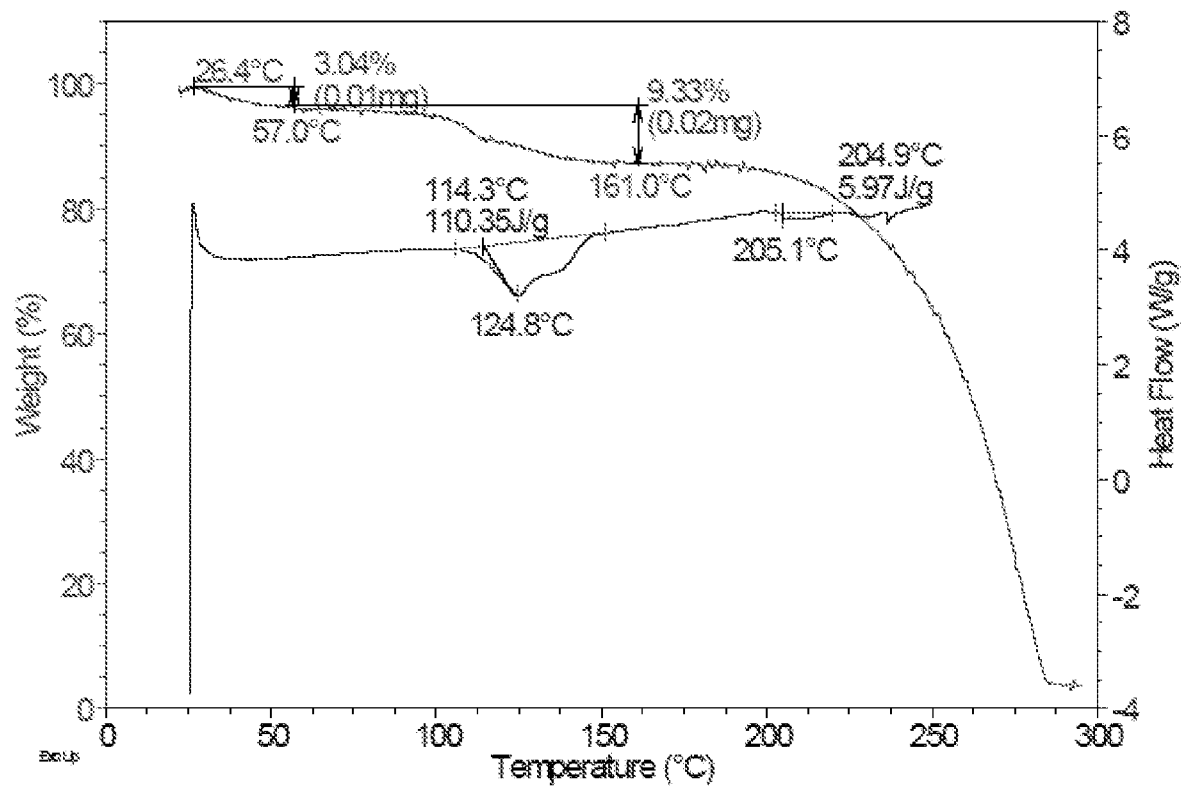
FIG. 2 provides a differential scanning calorimetry (DSC) profile and thermal gravimetric analysis (TGA) profile of Form G of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In another embodiment, Form G is characterized by the DSC spectrum shown in FIG. 2. The DSC graph plots the heat flow as a function of temperature from a sample, the temperature rate change being about 10° C./min. The DSC profile is characterized by two endotherms at 114.3° C. and 204.9° C. (onset temperature).

Figure 3:
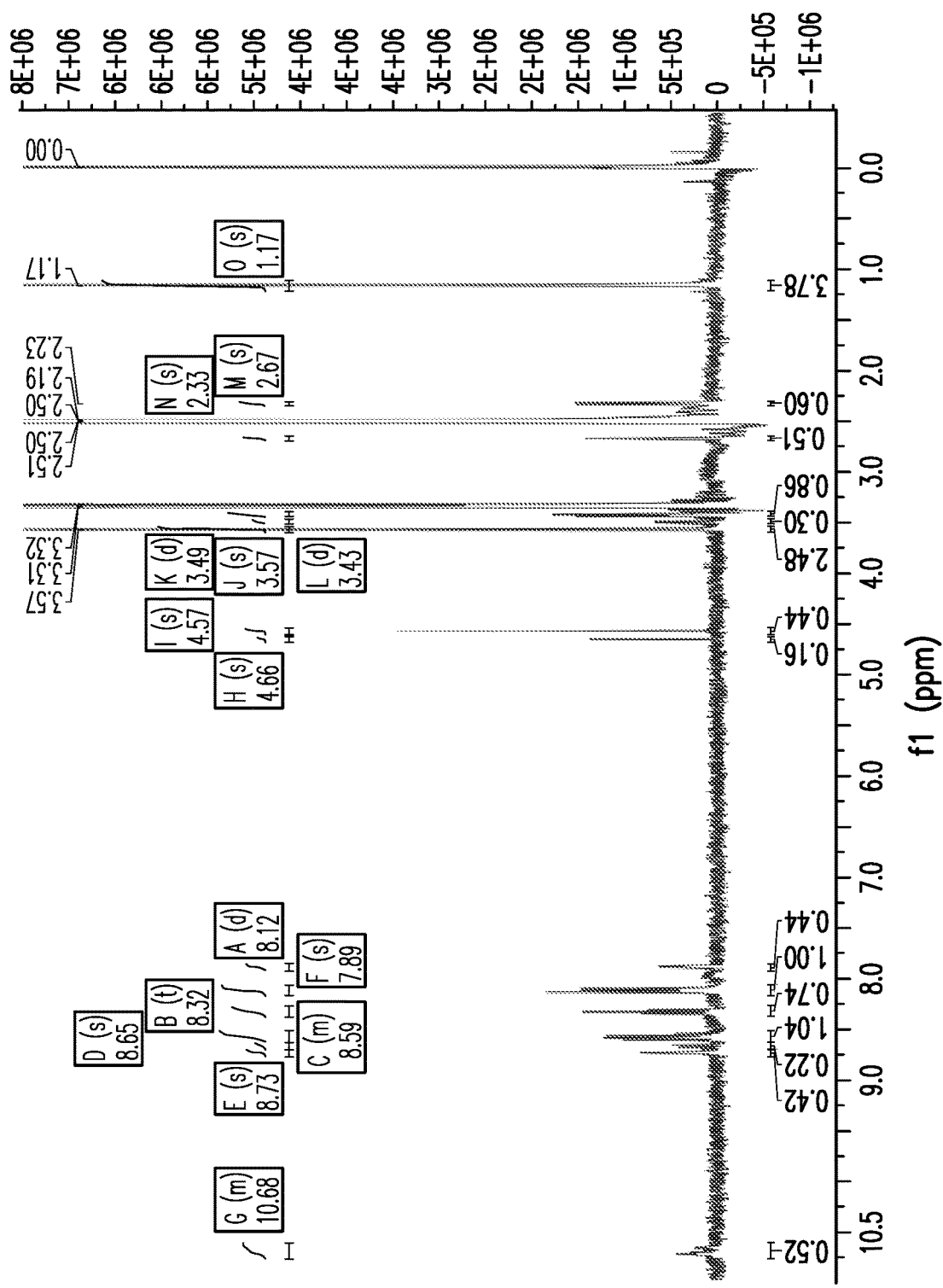
FIG. 3 provides a $^1$H NMR (400 MHz, DMSO-d6) spectrum of Form G of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In another embodiment, Form G is characterized by the TGA profile shown in FIG. 2. The TGA profile graphs the percent loss of weight of the sample as a function of temperature, the temperature rate change being about 10° C./min. The weight loss represents a loss of about 12.4% of the weight of the sample as the temperature is increased to about 161.0° C. When heated to 160° C., Type G converted to an amorphous solid, as shown in FIG. 1. FIG. 3 provides the $^1$H NMR spectrum, which indicates that the molar ratio of dioxane to 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is 0.5.

Form H

Figure 4:
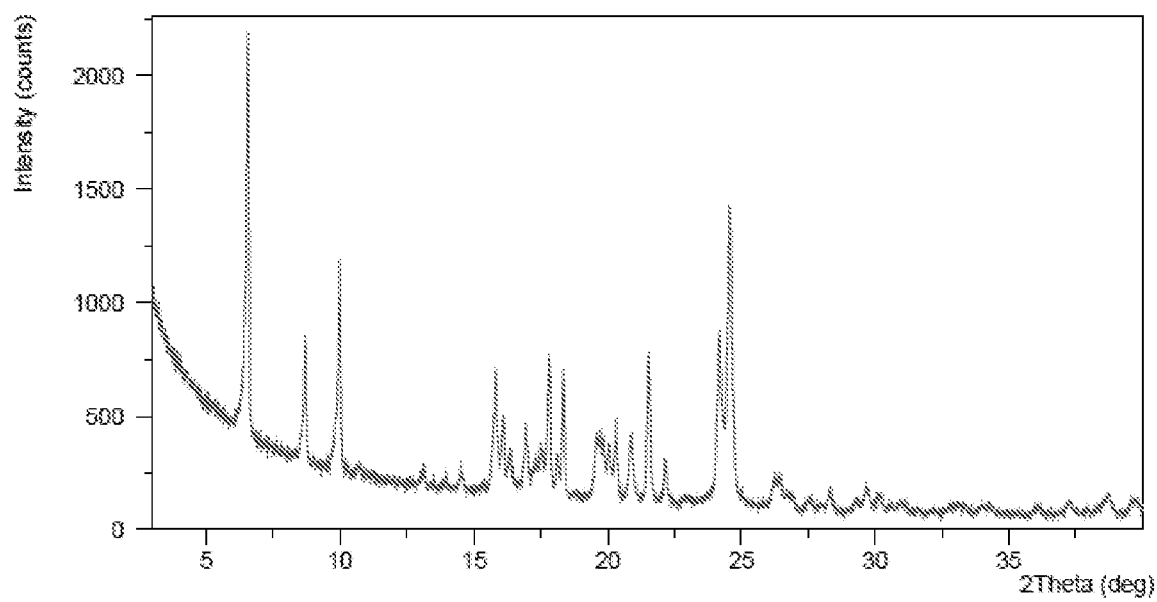
FIG. 4 provides an X-ray powder diffractogram (XRPD) of Form H of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In one embodiment, a single crystalline form, Form H, of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is characterized by the X-ray powder diffraction (XRPD) pattern shown in FIG. 4, and data shown in Table 2, obtained using CuKα radiation. In a particular embodiment, the polymorph can be characterized by one or more of the peaks taken from FIG. 4. In one embodiment, the polymorph can be characterized by an X-ray powder diffraction pattern comprising peaks at about 6.56 and 9.99° 2θ. In one embodiment, the polymorph can be characterized by an X-ray powder diffraction pattern comprising peaks at about 6.56, 9.99, 24.17 and 24.56° 2θ. In one embodiment, the polymorph can be characterized by an X-ray powder diffraction pattern comprising one or two or three or four or five or more of the peaks shown in Table 2.

TABLE 2

Peak List for Form H

| Angle (° 2θ) | Relative Intensity |
| --- | --- |
| 3.064602 | 21.39 |
| 6.564487 | 100.00 |
| 8.708494 | 32.35 |
| 9.999902 | 52.68 |
| 15.801420 | 30.37 |
| 16.098050 | 19.23 |
| 16.943730 | 16.73 |
| 17.516640 | 11.91 |
| 17.814680 | 35.69 |
| 18.352120 | 33.14 |
| 19.576400 | 14.90 |
| 20.050790 | 13.98 |
| 20.300820 | 20.44 |
| 20.873130 | 15.56 |
| 21.535720 | 39.02 |
| 24.169040 | 43.65 |
| 24.563650 | 76.01 |

Figure 5:
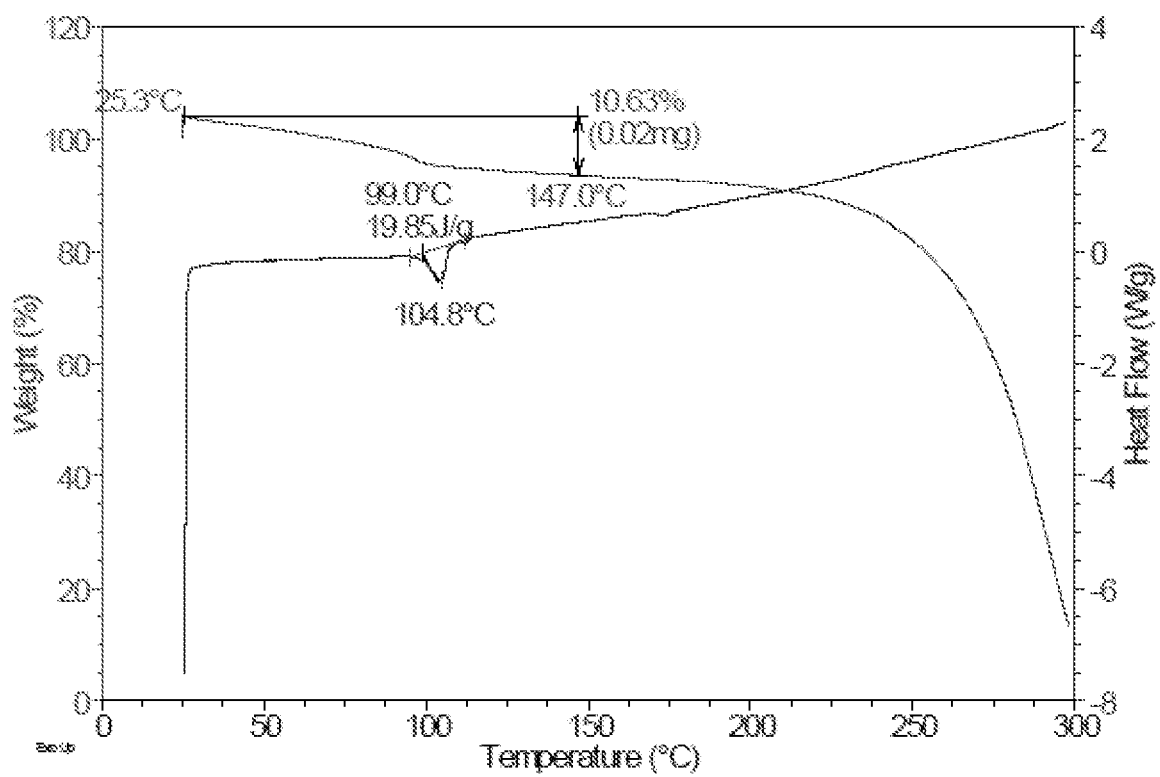
FIG. 5 provides a differential scanning calorimetry (DSC) profile and thermal gravimetric analysis (TGA) profile of Form H of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In another embodiment, Form H is characterized by the DSC spectrum shown in FIG. 5. The DSC graph plots the heat flow as a function of temperature from a sample, the temperature rate change being about 10° C./min. The DSC profile is characterized by one endotherm at 99.0° C. (onset temperature).

Figure 6:
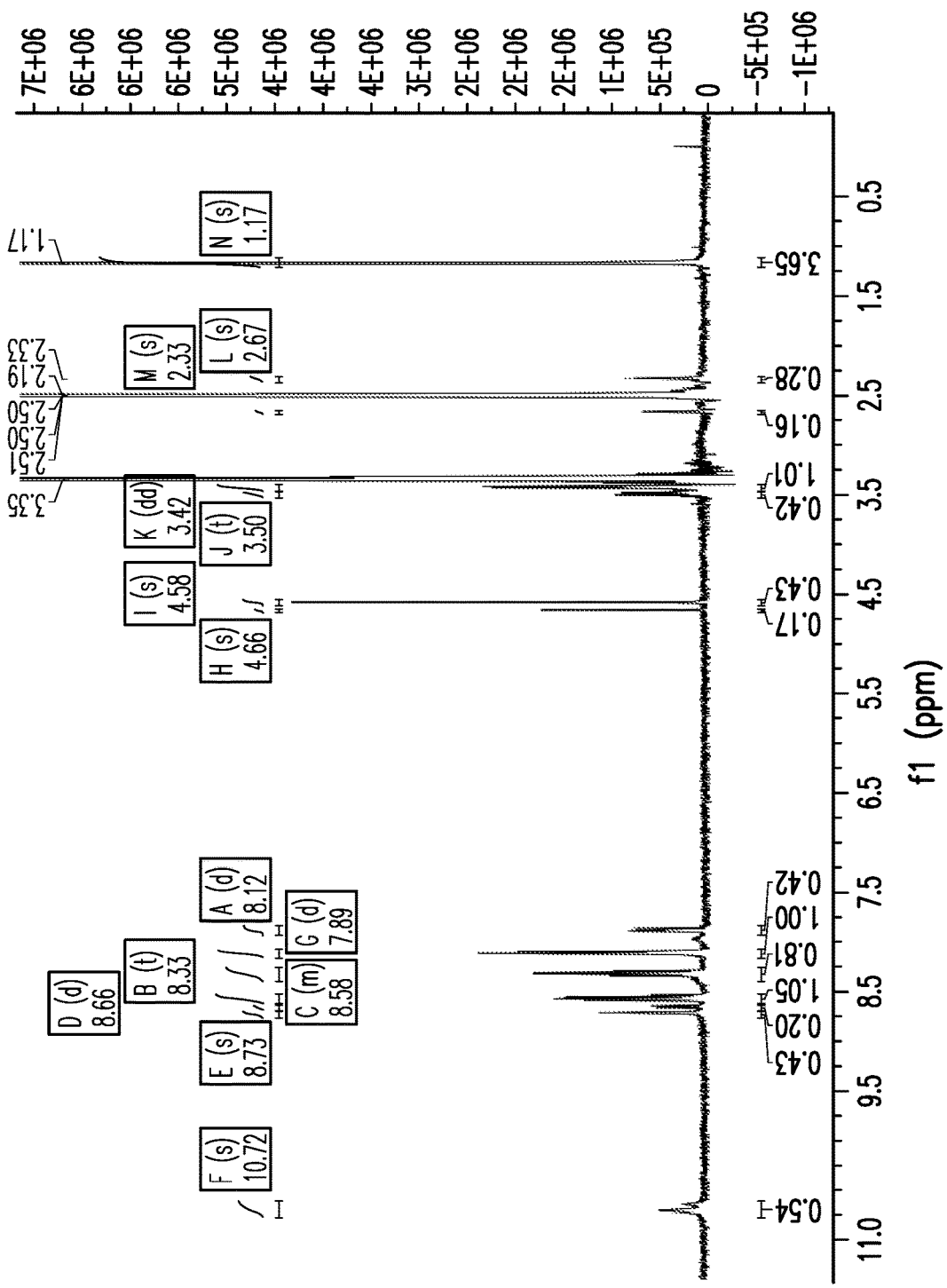
FIG. 6 provides a $^1$H NMR (400 MHz, DMSO-d6) spectrum of Form H of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In another embodiment, Form H is characterized by the TGA profile shown in FIG. 5. The TGA profile graphs the percent loss of weight of the sample as a function of temperature, the temperature rate change being about 10° C./min. The weight loss represents a loss of about 10.6% of the weight of the sample as the temperature is increased to about 147.0° C. FIG. 6 provides the $^1$H NMR spectrum, which indicates no residual solvent.

Form J

Figure 7:
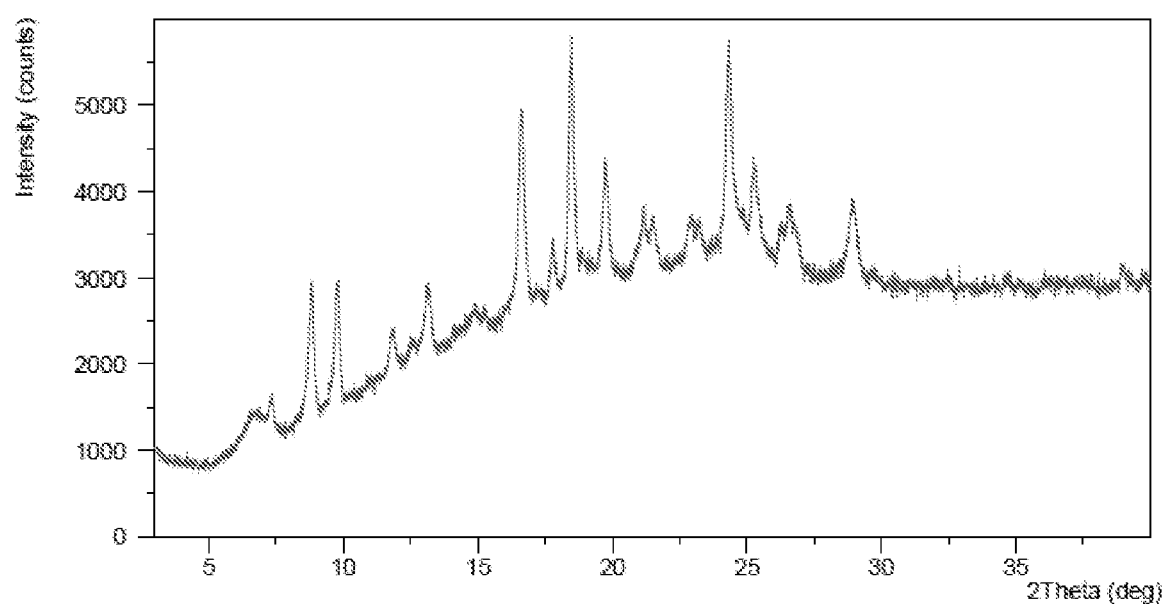
FIG. 7 provides an X-ray powder diffractogram (XRPD) of Form J of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In one embodiment, a single crystalline form, Form J, of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is characterized by the X-ray powder diffraction (XRPD) pattern shown in FIG. 7, and data shown in Table 3, obtained using CuKα radiation.

In one embodiment, the polymorph can be characterized by one or more of the peaks taken from FIG. 7, as shown in Table 3. In one embodiment, the polymorph can be characterized by an X-ray powder diffraction pattern comprising peaks at about 16.58, 18.49, and 24.32° 2θ. In one embodiment, the polymorph can be characterized by an X-ray powder diffraction pattern comprising peaks at about 16.58, 18.49, 19.74 and 24.32° 2θ. In one embodiment, the polymorph can be characterized by an X-ray powder diffraction pattern comprising one or two or three or four or five or six or seven or eight or nine of the peaks shown in Table 3.

TABLE 3

Peak List for Form J

| Angle (° 2θ) | Relative Intensity |
| --- | --- |
| 6.669287 | 12.36 |
| 7.362828 | 15.36 |
| 8.805528 | 48.94 |
| 9.741103 | 46.69 |
| 11.845000 | 26.41 |
| 12.516040 | 22.36 |
| 13.128820 | 38.07 |
| 14.830200 | 27.10 |
| 16.581920 | 83.56 |
| 17.779710 | 41.55 |
| 18.485790 | 100.00 |
| 19.740550 | 63.29 |
| 21.153070 | 44.60 |
| 21.526250 | 41.33 |
| 22.898060 | 38.14 |
| 23.239420 | 36.71 |
| 24.315940 | 89.79 |
| 25.284490 | 48.52 |
| 26.602960 | 34.17 |
| 28.953730 | 28.71 |

Form K

Figure 9:
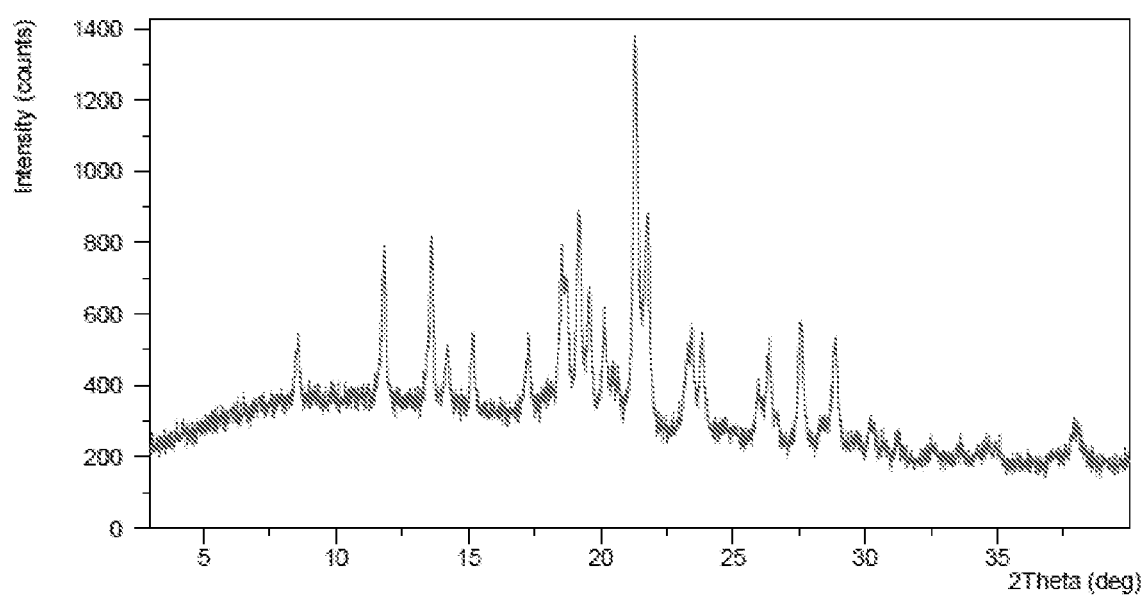
FIG. 9 provides an X-ray powder diffractogram (XRPD) of Form K of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In one embodiment, a single crystalline form, Form K, of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is characterized by the X-ray powder diffraction (XRPD) pattern shown in FIG. 9, and data shown in Table 4, obtained using CuKα radiation.

In one embodiment, the polymorph can be characterized by one or more of the peaks taken from FIG. 9, as shown in Table 4. In one embodiment, the polymorph can be characterized by an X-ray powder diffraction pattern comprising peaks at about 21.29 and 21.79° 2θ. In one embodiment, the polymorph can be characterized by an X-ray powder diffraction pattern comprising peaks at about 13.62, 19.19, 21.29, and 21.79° 2θ. In one embodiment, the polymorph can be characterized by an X-ray powder diffraction pattern comprising one or two or three or four or five or six or seven or eight or nine of the peaks shown in Table 4.

TABLE 4

Peak List for Form K

| Angle (° 2θ) | Relative Intensity |
| --- | --- |
| 8.557263 | 16.05 |
| 11.835550 | 36.02 |
| 13.629920 | 43.94 |
| 14.225330 | 14.99 |
| 15.171130 | 20.09 |
| 17.292910 | 19.23 |
| 18.531480 | 41.06 |
| 18.734230 | 35.99 |
| 19.190100 | 52.56 |
| 19.592320 | 33.37 |
| 20.145700 | 24.91 |
| 21.299430 | 100.00 |
| 21.792120 | 54.41 |
| 23.445660 | 26.50 |
| 23.821150 | 25.70 |
| 25.970100 | 13.81 |
| 26.395330 | 23.02 |
| 27.554740 | 31.22 |
| 28.868860 | 27.59 |

Figure 10:
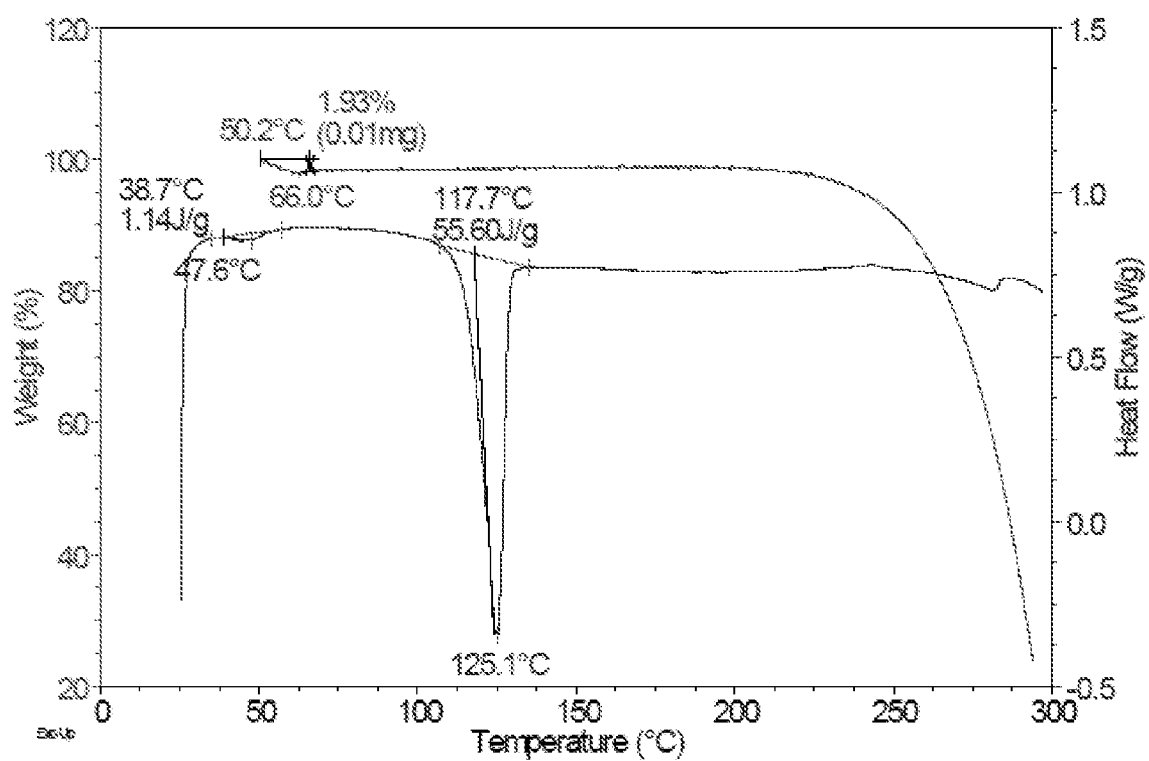
FIG. 10 provides a differential scanning calorimetry (DSC) profile and thermal gravimetric analysis (TGA) profile of Form K of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In another embodiment, Form K is characterized by the DSC profile shown in FIG. 10. The DSC graph plots the heat flow as a function of temperature from a sample, the temperature rate change being about 10° C./min. The DSC profile is characterized by two endotherms at 38.7° C. and 117.7° C. (onset temperature).

In another embodiment, Form K is characterized by the TGA profile shown in FIG. 10. The TGA profile graphs the percent loss of weight of the sample as a function of temperature, the temperature rate change being about 10° C./min. In one embodiment, Form K shows a weight loss of ~1.9% when temperature is raised to about 66° C.

Provided herein is an assortment of characterizing information to describe the solid forms provided herein. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present. The XRPD peaks described in Tables 1 to 4 may vary by +0.2° 2θ depending upon the method and instrument used to obtain the data. The intensity of the XRPD peaks described in Tables 1 to 4 may vary by 10% or more.

The characterization of a solid form may be by any combination of one or more of the XRPD, TGA, and DSC, described for a particular solid form. For example, a single crystalline form may be characterized by any combination of the XRPD results regarding the position of the major peaks in a XRPD scan; and/or any combination of one or more of parameters derived from data obtained from a XRPD scan. A single crystalline form may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule as determined by water sorption/desorption measurements over a range of relative humidity (e.g., 0% to 90%) may also characterize a single crystalline form provided herein.

The combinations of characterizations that are discussed above may be used to describe any of the polymorphs provided herein.

The solid forms provided herein have physical properties that are suitable for large scale pharmaceutical formulation manufacture, for example, high crystallinity, high melting point, and limited occluded or solvated solvent. In certain embodiments, the solid forms provided herein have improved bioavailability as compared to amorphous forms.

Compositions Containing the Solid Forms and Routes of Administration

In certain embodiments, the solid forms provided herein are formulated using the techniques similar to those described in US Application Publication No. US 2018/0064715 A1, incorporated herein by reference in its entirety.

In one embodiment, the formulations provided herein comprise a solid form described herein in a tablet as described in IDHIFA® label issued August 2017, available at https://www.accessdata.fda.gov/drugsatfda_docs/label/2017/209606s000lbl.pdf.

In one embodiment, the solid forms provided herein are formulated with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as TWEENs or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the solid forms described herein.

In one embodiment, the pharmaceutical composition comprises a solid form provided herein and an excipient. In one embodiment, the pharmaceutical composition that comprises a solid form provided herein and an excipient, is for oral administration. In one embodiment, the excipient is a diluent, a binder, a disintegrant, a wetting agent, a stabilizer, a glidant, or a lubricant.

In one embodiment, the diluent is a microcrystalline cellulose.

In one embodiment, the binder is a hydroxypropyl cellulose.

In one embodiment, the disintegrant is sodium starch glycolate.

In one embodiment, the wetting agent is sodium lauryl sulfate.

In one embodiment, the stabilizer is hypromellose acetate succinate.

In one embodiment, the glidant is colloidal silicon dioxide.

In one embodiment, the lubricant is magnesium stearate.

Oral delivery formats include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains a solid form provided herein.

Certain embodiments herein provide solid oral dosage forms that are tablets or capsules. In certain embodiments, the formulation is a tablet comprising a solid form provided herein. In certain embodiments, the formulation is a capsule comprising a solid form provided herein. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration.

In one embodiment, provided are pharmaceutical formulations (e.g., immediate release oral formulations and/or formulations that release 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol substantially in the stomach) comprising a solid form provided herein that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol substantially in the stomach) comprising a solid form provided herein that achieve a particular maximum plasma concentration ("Cmax") in the subject to which the formulation is orally administered. Particular embodiments provide oral formulations that achieve a Cmax of 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol substantially in the stomach) comprising a solid form provided herein that achieve a particular time to maximum plasma concentration ("Tmax") in the subject to which the formulation is orally administered. Particular embodiments provide oral formulations that achieve a Tmax of 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising a solid form provided herein wherein the oral dosage forms have an enteric coating. Particular embodiments provide a permeable or partly permeable (e.g., "leaky") enteric coating with pores. In particular embodiments, the permeable or partly permeable enteric-coated tablet releases 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol in an immediate release manner substantially in the stomach.

Provided herein are dosage forms designed to maximize the absorption and/or efficacious delivery of 2-methyl-1-[(4-[6-(trifluoromethyl)pyridin-2-yl]-6-{[2-(trifluoromethyl) pyridin-4-yl]amino}-1,3,5-triazin-2-yl)amino]propan-2-ol, upon oral administration, e.g., for release substantially in the stomach. Accordingly, certain embodiments herein provide a solid oral dosage form comprising a solid form provided herein using pharmaceutical excipients designed for immediate release of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol upon oral administration, e.g., substantially in the stomach. Particular immediate release formulations comprise a specific amount of a solid form provided herein and optionally one or more excipients. In certain embodiments, the formulation may be an immediate release tablet or an immediate release capsule (such as, e.g., an HPMC capsule).

Provided herein are methods of making the formulations provided herein comprising a solid form provided herein (e.g., immediate release oral formulations and/or formulations that release 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol substantially in the stomach, or rapidly disintegrating formulations that dissolve substantially in the mouth) comprise a solid form provided herein in a specific amount. In particular embodiments, the specific amount of a solid form provided in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment, the specific amount is about 140 mg. In one embodiment, the specific amount is about 150 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising a solid form provided herein alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of a solid form provided herein and vegetable oil or non-aqueous, water miscible materials such as, for example, polyethylene glycol and the like. In certain embodiments, hard gelatin capsules may be prepared containing granules of a solid form provided herein in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of a solid form provided herein is prepared using aqueous solvents without causing significant hydrolytic degradation of the compound. In particular embodiments, the formulation is a tablet which contains a coating applied to the drug core using aqueous solvents without causing significant hydrolytic degradation of the compound in the formulation. In certain embodiments, water is employed as the solvent for coating the drug core. In certain embodiments, the oral dosage form of a solid form provided herein is a tablet containing a film coat applied to the drug core using aqueous solvents. In particular embodiments, water is employed as the solvent for film-coating. In particular embodiments, the tablet containing a solid form provided herein is film-coated using aqueous solvents without effecting degradation of the pharmaceutical composition. In particular embodiments, water is used as the film coating solvent without effecting degradation of the pharmaceutical composition. In certain embodiments, an oral dosage form comprising a solid form provided herein and an aqueous film coating effects immediate drug release upon oral delivery. In certain embodiments, the oral dosage form comprising a solid form provided herein and an aqueous film coating effects controlled drug release to the upper gastrointestinal tract, e.g., the stomach, upon oral administration. In particular embodiments, a tablet with an aqueous-based film coating comprises a solid form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol as the API.

In certain embodiments, provided herein is a controlled release pharmaceutical formulation for oral administration of a solid form provided herein, wherein the release occurs substantially in the stomach, comprising: a) a specific amount of a solid form provided herein; b) a drug release controlling component for controlling the release of a solid form provided herein substantially in the upper gastrointestinal tract, e.g., the stomach; and c) optionally one or more excipients. In certain embodiments, the oral dosage form comprising a solid form provided herein is prepared as a controlled release tablet or capsule which includes a drug core comprising the pharmaceutical composition and optional excipients. Optionally, a "seal coat" or "shell" is applied. In certain embodiments, a formulation provided herein comprising a solid form provided herein is a controlled release tablet or capsule, which comprises a therapeutically effective amount of a solid form provided herein, a drug release controlling component that controls the release of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol from the polymer matrix substantially in the stomach. In certain embodiments, such formulations may be prepared by incorporating a solid form provided herein into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045,823); Gusler et al., U.S. Patent Publication No. 2003/0104053 (application Ser. No. 10/029,134), each of which is incorporated herein by reference in its entirety.

In certain embodiments, the drug release controlling component may comprise a shell surrounding the drug-containing core, wherein the shell releases 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol from the core by, e.g., permitting diffusion of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol from the core and promoting gastric retention of the formulation by swelling upon exposure to gastric fluids to a size that is retained in the stomach. In certain embodiments, such formulations may be prepared by first compressing a mixture of a solid form provided herein and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain a solid form provided herein and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, carbomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sulfobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In certain embodiments, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, TWEEN 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs or SPANs and/or other similar emulsifying agents or bioavailability enhancers which are commonly used in the manufacture of pharmaceutically acceptable solid, liquid, or other dosage forms may also be used for the purposes of formulation.

In certain embodiments, the pharmaceutical compositions provided herein may also be administered in the form of suppositories for rectal administration. These compositions can be prepared by mixing a solid form provided herein with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. In certain embodiments, carriers for topical administration of the compounds provided herein include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In certain embodiments, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In certain embodiments, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Methods of Use

In one embodiment, provided herein are methods of treating or ameliorating one or more symptoms of a disease selected from a hematological malignancy and a solid tumor, each characterized by the presence of a mutant allele of IDH2, comprising administering to a subject having the disease a therapeutically effective amount of a solid form or a pharmaceutical composition comprising the solid form provided herein. In one embodiment, the disease is relapsed or refractory. In one embodiment, the subject is a pediatric patient.

In one embodiment, the solid forms provided herein are useful for treating or preventing a disease/disorder, or are useful to lessen the severity of a disease/disorder, wherein the disease/disorder is selected from AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, or cholangiocarcinoma, each characterized by the presence of a mutant allele of IDH2. In one embodiment, the solid form is Form G. In another embodiment the solid form is Form H. In yet another embodiment, the solid form is Form J. In still another embodiment the solid form is Form K.

In one embodiment, provided herein is a method of treating, preventing, or ameliorating one or more symptoms of a disease or condition, comprising the administration of a solid form provided herein, wherein the disease or condition is selected from AML, MDS, CMML, myeloid sarcoma, multiple myeloma, lymphoma (e.g., T-cell lymphoma and B-cell lymphoma), AITL, blastic plasmacytoid dendritic cell neoplasm, MPN, glioma, melanoma, chondrosarcoma, and cholangiocarcinoma, each characterized by the presence of a mutant allele of IDH2. In one embodiment, the disease or condition is AML, characterized by the presence of a mutant allele of IDH2. In one embodiment, the disease or condition is AML, characterized by the presence of a mutant allele of IDH2. In one embodiment, the disease or condition is MDS, characterized by the presence of a mutant allele of IDH2.

In one embodiment, the mutant allele of IDH2 has an R140X mutation. In another embodiment, the R140X mutation is a R140Q mutation. In another embodiment, the R140X mutation is a R140W mutation. In another embodiment, the R140X mutation is a R140L mutation. In another embodiment, the mutant allele of IDH2 has an R172X mutation. In another embodiment, the R172X mutation is a R172K mutation. In another embodiment, the R172X mutation is a R172G mutation. A cancer selected from AML, MDS, CMML, myeloid sarcoma, multiple myeloma, lymphoma (e.g., T-cell lymphoma and B-cell lymphoma), AITL, blastic plasmacytoid dendritic cell neoplasm, MPN, glioma, melanoma, chondrosarcoma, and cholangiocarcinoma can be analyzed by sequencing cell samples to determine the presence and specific nature of a mutation (e.g., the changed amino acid present) at amino acid 140 and/or 172 of IDH2.

Without being bound by theory, applicants believe that mutant alleles of IDH2 wherein the IDH2 mutation results in a new ability of the enzyme to catalyze the NADPH-dependent reduction of α-ketoglutarate to R(−)-2-hydroxyglutarate, and in particular R140Q and/or R172K mutations of IDH2, characterize a subset of all types of cancers described herein, without regard to their cellular nature or location in the body. Thus, the methods of one aspect are useful to treat a hematological cancer selected from AML, MDS, CMML, myeloid sarcoma, multiple myeloma, lymphoma (e.g., T-cell lymphoma and B-cell lymphoma), AITL, blastic plasmacytoid dendritic cell neoplasm, MPN, glioma, melanoma, chondrosarcoma, and cholangiocarcinoma, that is characterized by the presence of a mutant allele of IDH2 imparting such activity and in particular an IDH2 R140Q and/or R172K mutation.

In one embodiment, the efficacy of treatment is monitored by measuring the levels of 2HG in the subject. Typically levels of 2HG are measured prior to treatment, wherein an elevated level is indicated for the use of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol to treat a disease selected from AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by the methods of PCT Publication No. WO 2013/102431 and US Publication No. US 2013/0190287 hereby incorporated by reference in their entirety, or by analogous methods well known to those of skill in the art.

In one embodiment 2HG is directly evaluated.

In another embodiment a derivative of 2HG formed in the process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

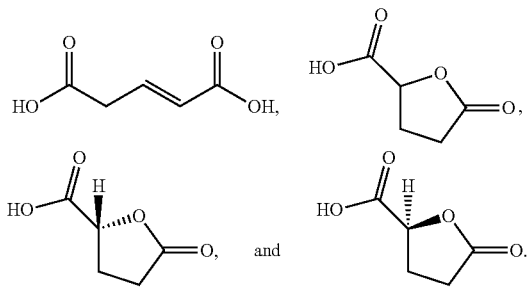

In one embodiment, the disease to be treated or whose one or more symptoms are to be ameliorated using the methods provided herein is selected from AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma, wherein at least 30, 40, 50, 60, 70, 80 or 90% of the tumor cells carry an IDH2 mutation, and in one embodiment an IDH2 R140Q, R140W, or R140L and/or R172K or R172G mutation, at the time of diagnosis or treatment.

In one embodiment, the method provided herein is a method of treating AML, characterized by the presence of a mutant allele of IDH2, selected from newly diagnosed AML, previously untreated AML, AML arising from MDS, AML arising from antecedent hematological disorder (AHD) and AML arising after exposure to genotoxic injury. In certain embodiments, the genotoxic injury is resulting from radiation and/or chemotherapy. In one embodiment, provided herein is a method of treating AML, characterized by the presence of a mutant allele of IDH2, arising after exposure to genotoxic injury resulting from radiation and/or chemotherapy.

In one embodiment, the method provided herein is a method of treating newly diagnosed AML, characterized by the presence of a mutant allele of IDH2.

In one embodiment, the method provided herein is a method of treating previously untreated AML, characterized by the presence of a mutant allele of IDH2.

In one embodiment, the method provided herein is a method of treating AML arising from MDS, characterized by the presence of a mutant allele of IDH2.

In one embodiment, the method provided herein is a method of treating AML arising from AHD, characterized by the presence of a mutant allele of IDH2.

In one embodiment, the method provided herein is a method of treating AML arising after exposure to genotoxic injury, characterized by the presence of a mutant allele of IDH2.

In some embodiments, the AML is relapsed and/or primary refractory AML, characterized by the presence of a mutant allele of IDH2. In some embodiments, the AML is relapsed and/or refractory AML, characterized by the presence of a mutant allele of IDH2. In one embodiment, the AML is refractory to one line of treatment (ie one previous treatment). In another embodiment, the AML is refractory to two lines of treatment.

In one embodiment, the method provided herein is a method of treating myeloproliferative neoplasm (MPN), characterized by the presence of a mutant allele of IDH2.

In another embodiment, the cancer to be treated is MDS, for example, MDS with refractory anemia with excess blasts (subtype RAEB-1 or RAEB-2), characterized by the presence of a mutant allele of IDH2. In other embodiments, the MDS is previously untreated. In one embodiment, the MDS is newly diagnosed MDS, characterized by the presence of a mutant allele of IDH2.

In another embodiment, the cancer to be treated is relapsed and/or primary refractory CMML, characterized by the presence of a mutant allele of IDH2.

In certain embodiments, the solid forms provided herein are for treating a hematological malignancy and a solid tumor, each characterized by the presence of a mutant allele of IDH2 and the absence of a mutant allele of FLT3 and/or a mutant allele of NRAS. In certain embodiments, the solid forms provided herein are for treating a hematological malignancy and a solid tumor, each characterized by the presence of a mutant allele of IDH2 and the absence of a mutant allele of FLT3. In certain embodiments, the solid forms provided herein are for treating a hematological malignancy and a solid tumor, each characterized by the presence of a mutant allele of IDH2 and the absence of a mutant allele of NRAS.

In certain embodiments, the solid forms provided herein are for treating a hematological malignancy characterized by the presence of a mutant allele of IDH2 and the absence of a mutant allele of FLT3 and/or a mutant allele of NRAS. Exemplary methods for treating a hematological malignancy characterized by the presence of a mutant allele of IDH2 and the absence of a mutant allele of FLT3 and/or a mutant allele of NRAS by administering 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol are described in US 2017/024617 and US 2017/0157132, the disclosure of each of which is incorporated herein by reference in its entirety.

In one embodiment, the solid forms provided herein are for treating a hematological malignancy characterized by the presence of a mutant allele of IDH2 and the absence of a mutant allele of FLT3. In one embodiment, the hematological malignancy is an advanced hematological malignancy. In one embodiment, the hematological malignancy is selected from acute myelogenous leukemia, myelodysplastic syndrome, chronic myelomonocytic leukemia, myeloid sarcoma, multiple myeloma, lymphoma, angioimmunoblastic T-cell lymphoma, blastic plasmacytoid dendritic cell neoplasm and myeloproliferative neoplasm. In one embodiment, the hematological malignancy is AML. In some embodiments, the AML is relapsed and/or refractory.

In one embodiment, provided herein are methods of treating a hematological malignancy by administering a solid form provided herein in combination with a therapeutically effective amount of one or more compounds that target a FLT3 pathway, wherein the hematological malignancy is characterized by the presence of a mutant allele of IDH2 and a mutant allele of FLT3, for example FLT3-ITD or FLT3-KDM. In one embodiment, the hematological malignancy is an advanced hematological malignancy. In one embodiment, the hematological malignancy is AML. In some embodiments, the AML is relapsed and/or refractory.

In one embodiment, provided herein is a method of treating hematological malignancies, such as AML, MDS, CMML, myeloid sarcoma, multiple myeloma, lymphoma (e.g., T-cell lymphoma or B-cell lymphoma), AITL, blastic plasmacytoid dendritic cell neoplasm or MPN, each characterized by the presence of a mutant allele of IDH2 and the absence of a mutant allele of FLT3, comprising administering a solid form provided herein. In one embodiment, the hematological malignancy is an advanced hematological malignancy. In one embodiment, the hematological malignancy is AML. In some embodiments, the AML is relapsed and/or refractory.

In one embodiment, provided herein is a method of treating hematological malignancies, such as AML, MDS, CMML, myeloid sarcoma, multiple myeloma, lymphoma (e.g., T-cell lymphoma or B-cell lymphoma), AITL, blastic plasmacytoid dendritic cell neoplasm, or MPN each characterized by the presence of a mutant allele of IDH2 and a mutant allele of FLT3, for example FLT3-ITD, comprising administering a solid form provided herein in combination with a therapeutically effective amount of one or more compounds that target a FLT3 pathway. Exemplary FLT3 inhibitors are described elsewhere herein. In one embodiment, the hematological malignancy is an advanced hematological malignancy. In one embodiment, the hematological malignancy is AML. In some embodiments, the AML is relapsed and/or refractory.

In one embodiment, provided herein are methods of treating solid tumors by administering a solid form provided herein, wherein the solid tumor is characterized by the presence of a mutant allele of IDH2 and the absence of a mutant allele of FLT3. In one embodiment, the solid tumor is an advanced solid tumor.

In one embodiment, provided herein are methods of treating solid tumors by administering to a subject a solid form provided herein in combination with a therapeutically effective amount of one or more compounds that target a FLT3 pathway, wherein the solid tumor is characterized by the presence of a mutant IDH2 and a mutant allele of FLT3, for example FLT3-ITD. In one embodiment, the solid tumor is an advanced solid tumor.

In one embodiment, provided herein is a method of treating solid tumors, such as glioma, melanoma, chondrosarcoma, or cholangiocarcinoma (e.g., glioma), or treating AITL, each characterized by the presence of a mutant allele of IDH2 and the absence of a mutant allele of FLT3, comprising administering to a subject a solid form provided herein.

In one embodiment, provided herein is a method of treating solid tumors, such as glioma, melanoma, chondrosarcoma, or cholangiocarcinoma (e.g., glioma), or treating AITL, each characterized by the presence of a mutant allele of IDH2 and a mutant allele of FLT3, in a subject comprising administering a solid form provided herein in combination with a therapeutically effective amount of one or more compounds that target a FLT3 pathway. Exemplary FLT3 inhibitors are described elsewhere herein.

In one embodiment, provided herein is a method of treating a hematological malignancy by administering a solid form provided herein, wherein the hematological malignancy is characterized by the presence of a mutant allele of IDH2 and the absence of a mutant allele of NRAS. In one embodiment, the hematological malignancy is an advanced hematological malignancy.

In one embodiment, provided herein is a method of treating a hematological malignancy by administering a solid form provided herein in combination with a therapeutically effective amount of one or more compounds that target RAS pathways, wherein the hematological malignancy is characterized by the presence of a mutant allele of IDH2 and a mutant allele of NRAS. In one embodiment, the hematological malignancy is an advanced hematological malignancy.

In one embodiment, provided herein is a method of treating a hematological malignancy, such as AML, MDS, CMML, myeloid sarcoma, multiple myeloma, lymphoma (e.g., T-cell lymphoma or B-cell lymphoma), AITL, blastic plasmacytoid dendritic cell neoplasm or MPN each characterized by the presence of a mutant allele of IDH2 and the absence of a mutant allele of NRAS, comprising administering a solid form provided herein. In one embodiment, the hematological malignancy is an advanced hematological malignancy.

In one embodiment, provided herein is a method of treating hematological malignancies, such as AML, MDS, CMML, myeloid sarcoma, multiple myeloma, lymphoma (e.g., T-cell lymphoma and B-cell lymphoma), AITL, blastic plasmacytoid dendritic cell neoplasm, MPN, glioma, melanoma, chondrosarcoma, and cholangiocarcinoma, each characterized by the presence of a mutant allele of IDH2 and a mutant allele of NRAS comprising administering a solid form provided herein in combination with a therapeutically effective amount of one or more compounds that target RAS pathways. In one embodiment, a solid form provided herein is administered to the subject in combination with a therapeutically effective amount of a MEK kinase inhibitor. Exemplary MEK kinase inhibitors are described elsewhere herein. In one embodiment, the hematological malignancy is an advanced hematological malignancy.

In one embodiment, provided herein are methods of treating solid tumors by administering a solid form provided herein, wherein the solid tumor is characterized by the presence of a mutant allele of IDH2 and the absence of a mutant allele of NRAS. In one embodiment, the solid tumor is an advanced solid tumor.

In one embodiment, provided herein are methods of treating solid tumors by administering a solid form provided herein in combination with a therapeutically effective amount of one or more compounds that target RAS pathways, wherein the solid tumor is characterized by the presence of a mutant IDH2 and a mutant allele of NRAS. In one embodiment, the solid tumor is an advanced solid tumor.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and the absence of a mutant allele of NRAS, comprising administering a solid form provided herein.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and a mutant allele of NRAS, comprising administering a solid form provided herein in combination with a therapeutically effective amount of one or more compounds that target RAS pathways.

In one embodiment, provided herein are methods of treating MPN in a subject comprising administering to the subject a solid form provided herein in combination with a therapeutically effective amount of a JAK2 inhibitor, wherein the subject harbors a mutant allele of IDH2 and a mutant allele of JAK2. Exemplary JAK2 inhibitors are described elsewhere herein.

In certain embodiments, provided herein is a method of treating a high risk MPN in a subject comprising administering to the subject a solid form provided herein in combination with a therapeutically effective amount of a JAK2 inhibitor, wherein the subject harbors a mutant allele of IDH2 and a mutant allele of JAK2.

In one embodiment, provided herein are methods of treating AML in a subject comprising administering to the subject a solid form provided herein in combination with a therapeutically effective amount of a JAK2 inhibitor, wherein the subject harbors a mutant allele of IDH2 and a mutant allele of JAK2. In some embodiments, the AML is relapsed and/or refractory.

In certain embodiments, the mutant allele of IDH2 is mIDH2-R140 or mIDH2-R172.

In certain embodiments, the mutant allele of IDH2 is mIDH2-R140Q, mIDH2-R140W, mIDH2-R140L, mIDH2-R172K, or mIDH2-R172G.

In certain embodiments, the mutant allele of JAK2 is mJAK2-V617F.

In certain embodiments, the solid forms provided herein are for treating MDS characterized by the presence of a mutant allele of IDH2 and a mutant allele of at least one second gene, wherein the second gene is selected from the group consisting of ASXL1 and SRSF2. In certain embodiments, the solid forms provided herein are for treating MDS characterized by the presence of a mutant allele of IDH2 and the absence of a mutant allele of at least one other gene, wherein the other gene is selected from the group consisting of KRAS, TP53, SETBP1, and U2AF1. In certain embodiments, the solid forms provided herein are for treating MDS characterized by the presence of a mutant allele of IDH2 and the absence of a mutant allele of at least one other gene, wherein the other gene is selected from the group consisting of KRAS, TP53, SETBP1, U2AF1, TCF3, STAG2, NRAS, JAK2 and BRAF. Exemplary methods of treating MDS characterized by the presence of a mutant allele of IDH2 by administering Compound 1 are described in US 2018/0042930-A1, the disclosure of which is incorporated herein by reference in its entirety.

In one embodiment, prior to and/or after treatment with a solid form provided herein, the method further comprises the step of evaluating the growth, size, weight, invasiveness, stage and/or other phenotype of the cancer selected from AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma.

In one embodiment, prior to and/or after treatment with a composition provided herein, the method further comprises the step of evaluating the IDH2 genotype of the cancer selected from AML, MDS, CMML, myeloid sarcoma, multiple myeloma, lymphoma (e.g., T-cell lymphoma or B-cell lymphoma), AITL, blastic plasmacytoid dendritic cell neoplasm, MPN, glioma, melanoma, chondrosarcoma, and cholangiocarcinoma. This may be achieved by ordinary methods in the art, such as DNA sequencing, immuno analysis, and/or evaluation of the presence, distribution or level of 2HG.

In one embodiment, prior to and/or after treatment with a composition provided herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as blood, plasma, urine, or spinal cord fluid analysis, or by analysis of surgical material, e.g., by mass-spectroscopy (e.g. LC-MS, GC-MS).

In one embodiment, the solid form provided herein is for use in any of the above described methods. In one embodiment, the solid form for use in the methods is a solid form provided herein. In one embodiment, the solid form for use in the methods is a mixture solid form provided herein.

In certain embodiments, depending on the disease to be treated and the subject's condition, the solid form provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The solid form provided herein may be formulated alone or together with one or more active agent(s), in suitable dosage unit with pharmaceutically acceptable excipients, carriers, adjuvants and vehicles, appropriate for each route of administration.

In certain embodiments, the amount of the solid form provided herein administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 60 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 60 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In certain embodiments, the solid form provided herein for methods described herein is administered at a dose of about 20 to 2000 mg/day. In certain embodiments, the solid form provided herein is administered at a dose of about 50 to 500 mg/day. In certain embodiments, the dose is about 60 mg/day. In certain embodiments, the dose is about 100 mg/day. In certain embodiments, the dose is about 150 mg/day. In certain embodiments, the dose is about 200 mg/day. In certain embodiments, the dose is about 300 mg/day.

In one embodiment, the amount of the solid form provided herein in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 30 mg. In one embodiment, the particular amount is about 50 mg. In one embodiment, the particular amount is about 60 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 650 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 60 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, the solid form provided herein can be delivered as a single dose such as, e.g., a single bolus injection, or oral tablets or pills; or over time such as, e.g., continuous infusion over time or divided bolus doses over time. In one embodiment, the solid form provided herein can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, the solid form provided herein for methods described herein is administered once daily.

In certain embodiments, the solid form provided herein is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering the solid form provided herein in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In certain embodiments, the solid form provided herein for methods described herein is administered for 1 to 25 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of the solid form provided herein administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In certain embodiments, the solid form provided herein is administered in one or more 28 day cycles in the methods described herein. In certain embodiments, the solid form provided herein is administered in a 28 day cycle in the methods described herein.

In certain embodiments, the solid form provided herein is administered orally in the methods described herein.

In certain embodiments, the solid form provided herein is administered once daily orally in 28-day cycles at the dose of about 100 mg/day in the methods described herein.

Combination Therapy

In certain embodiments, the solid forms provided herein are used with an additional cancer therapeutic agent or an additional cancer treatment. Exemplary additional cancer therapeutic agents and additional cancer treatments are described in US 2013/0190287, US 2017/0157132, US 2017/0246174, WO 2017/066611, and WO 2017/066599, and International Application No. PCT/US18/31090, the disclosures of each of which is incorporated herein by reference in their entireties.

In certain embodiments, additional cancer therapeutic agents include for example, chemotherapy, targeted therapy, antibody therapies, immunotherapy, and hormonal therapy. In certain embodiments, additional cancer treatments include, for example: surgery, and radiation therapy. Examples of each of these treatments are provided below.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone methylation inhibitors (such as azacytidine (e.g. Vidaza®); histone deacetylase inhibitors HDACs, such as butyrates (e.g., sodium phenylbutyrate)); hybrid polar compounds (such as hexamethylene bisacetamide ((HMIIBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin dependent kinase inhibitors such as Alvocidib and Seliciclib. Monoclonal antibody therapy is another strategy in which the therapeutic agent is an antibody which specifically binds to a protein on the surface of the cancer cells. Examples include the anti HER2/neu antibody trastuzumab (HERCEPTIN®) typically used in breast cancer, and the anti CD20 antibody rituximab and Tositumomab typically used in a variety of B cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft versus tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

In one embodiment, the compositions provided herein are used for treatment of AML in combination with an AML induction and consolidation therapy. In one embodiment, the AML induction therapy is a combination of cytarabine and daunorubicin. In one embodiment, the AML induction therapy is a combination of cytarabine and idarubicin.

In one embodiment, the AML consolidation therapy is cytarabine. In one embodiment, the AML consolidation therapy is a combination of mitoxantrone and etoposide.

In one embodiment, the compositions provided herein are used in combination with one or more DNA demethylating agents. In one embodiment, the DNA demethylating agent is a cytidine analog. In certain embodiments, the cytidine analog is azacitidine or 5-aza-2'-deoxycytidine (decitabine). In certain embodiments, the cytidine analog is azacitidine. In certain embodiments, the cytidine analog is 5-aza-2'-deoxycytidine (decitabine). In certain embodiments, the cytidine analog is, for example: 1-β-D-arabinofuranosylcytosine (cytarabine or ara-C); pseudoiso-cytidine (psi ICR); 5-fluoro-2'-deoxycytidine (FCdR); 2'-deoxy-2',2'-difluorocytidine (gemcitabine); 5-aza-2'-deoxy-2',2'-difluorocytidine; 5-aza-2'-deoxy-2'-fluorocytidine; 1-β-D-ribofuranosyl-2(1H)-pyrimidinone (zebularine); 2',3'-dideoxy-5-fluoro-3'-thiacytidine (emtriva); 2'-cyclocytidine (ancitabine); 1-β-D-arabinofuranosyl-5-azacytosine (fazarabine or ara-AC); 6-azacitidine (6-aza-CR); 5,6-dihydro-5-azacitidine (dH-aza-CR); $N^4$ pentyloxy-carbonyl-5'-deoxy-5-fluorocytidine (capecitabine); $N^4$ octadecyl-cytarabine; or elaidic acid cytarabine. In certain embodiments, the cytidine analogs include any compound which is structurally related to cytidine or deoxycytidine and functionally mimics and/or antagonizes the action of cytidine or deoxycytidine.

In one embodiment, the compositions provided herein are used in combination with azacitidine.

In one embodiment, the compositions provided herein are used in combination with a FLT3 inhibitor. In one embodiment, the FLT3 inhibitor is selected from quizartinib (AC220), sunitinib (SU11248), sorafenib (BAY 43-9006), midostaurin (PKC412), crenolanib (CP-868596), PLX3397, E6201, AKN-028, ponatinib (AP24534), ASP2215, KW-2449, famitinib and DCC-2036.

In one embodiment, the compositions provided herein are used in combination with MEK kinase inhibitor. In one embodiment, the MEK kinase is selected from trametinib, selumetinib, binimetinib, PD-325901, cobimetinib, CI-1040 and PD035901.

In one embodiment, the compositions provided herein are used in combination with a JAK inhibitor. In one embodiment, the compositions provided herein are used in combination with a JAK2 inhibitor. In one embodiment, the JAK2 inhibitor is selected from INCB018424 (ruxolitinib), TG101348, CYT387, AZD1480, SB1518 (pacritinib), XL019, NCB0-16562, NVP-BSK805, R723, hydroxycarbamide, SAR302503, CP-690,550 (tasocitinib) and INCB16562. In one embodiment, the compositions provided herein are used in combination with ruxolitinib.

These methods of treatment and pharmaceutical compositions are further illustrated by the detailed descriptions and illustrative examples given below.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

EXAMPLES

The embodiments described below are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

The following abbreviations are used:
ca approximately
DSC differential scanning calorimetry
DVS dynamic vapor sorption
HPLC high performance liquid chromatography
min minutes
NMR nuclear magnetic resonance
RH relative humidity
TGA thermal gravimetric analysis
XRPD X-ray powder diffraction General Methods
XRPD
For XRPD analysis, a PANalytical Empyrean X-ray powder diffractometer (XRPD) was used. The actual XRPD parameters used are listed in Table 5:

| Parameters for Reflection Mode | |
| --- | --- |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2θ) | 3°-40° |
| Step size (°2θ) | 0.0130 |
| Scan speed (°/min) | About 10 |

Differential Scanning Calorimetry (DSC)
For DSC, TA Q200 DSC from TA Instruments was used.
Temperature was ramped from room temperature to the desired temperature at a heating rate of 10° C./min using $N_2$ as the purge gas, with pan crimped.

Thermogravimetric Analysis (TGA)
For TGA, TA Q500 TGA from TA Instruments was used.
Temperature was ramped from room temperature to the desired temperature at a heating rate of 10° C./min using $N_2$ as the purge gas.

Dynamic Vapor Sorption Analysis (DVS)
Dynamic Vapor Sorption (DVS) was measured via a SMS (Surface Measurement Systems) DVS Intrinsic. The relative humidity at 25° C. were calibrated against deliquescence point of LiCl, $Mg(NO_3)_2$ and KCl. Typical Parameters for DVS test were listed in Table 6.

TABLE 6

| Parameters for DVS test | |
| --- | --- |
| Parameters | Value |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 20% RH-95% RH-0% RH-95% RH |
| RH step size | 10% (20% RH-90% RH-0% RH-90% RH) 5% (90% RH-95% RH-90% RH) |

Starting Materials
The starting materials used in the Examples below were polymorph Forms 1, 2 and 19 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, obtained by methods known to one of skill in the art, for example methods described in U.S. Pat. No. 9,738,625.

Example 1: Synthesis of Form G 10 mg of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, Form 1 (disclosed in WO 2015/017821 at page nos. 43-44 and 72) was dissolved in 1 mL dioxane to obtain a clear solution, followed by addition of 4 mL n-heptane. After stirring for about 24 hours, a precipitate was isolated. The precipitate was analyzed by XRPD. The crystalline form obtained was dioxane solvate Form G.

Polymorph Form G is characterized by the XRPD pattern provided in FIG. 1.

The DSC spectrum of Form G, provided in FIG. 2, shows endotherms at 114.3° C. and 204.9° C. (onset temperature).

The TGA profile of Form G, provided in FIG. 2, shows a loss of about 12.4% of the weight of the sample as the temperature iwa increased to about 160.0° C. When heated to 160° C., Type G converted to an amorphous solid, as shown in FIG. 1. FIG. 3 provides the $^1H$ NMR spectrum, which indicated that the molar ratio of dioxane to Form G is 0.5.

Example 2: Synthesis of Form H 10 mg of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, Form 1 was dissolved in 4 mL methanol to obtain a clear solution, followed by addition of 3 mL water. After stirring for about 24 hours, a precipitate was isolated.

Polymorph Form H is characterized by the XRPD pattern provided in FIG. 4.

The DSC spectrum of Form H, provided in FIG. 5, shows one endotherm at 99.0° C. (onset temperature).

The TGA profile of Form H, provided in FIG. 5, shows a loss of about 10.6% of the weight of the sample as the temperature was increased to about 147.0° C. FIG. 6 provides the $^1H$ NMR spectrum of Form H, which indicates no residual solvent.

Example 3: Synthesis of Form J

Figure 8:
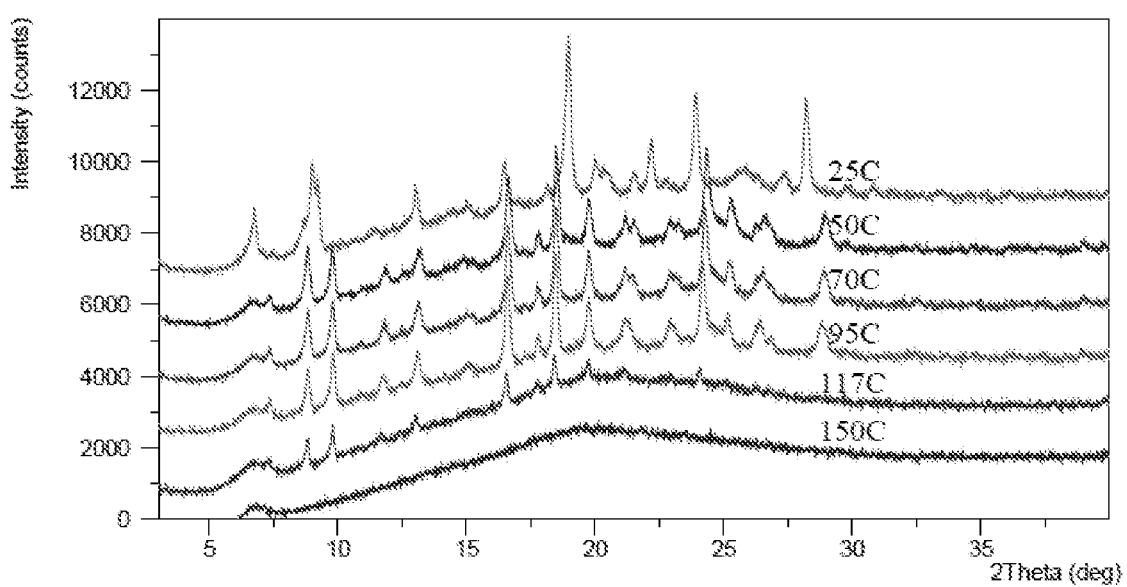
FIG. 8 provides a variable temperature XRPD pattern for a mixture of Form 1 and Form 19 of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

A mixture of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, Form 1 and Form 19 (disclosed in WO 2015/017821 at page nos. 62 and 76) was heated to 50° C. using variable temperature XRPD method to obtain Form J. A variable temperature XRPD pattern for the mixture of Forms 1 and 19 used to prepare Form J is provided in FIG. 8.

Polymorph Form J is characterized by the XRPD pattern provided in FIG. 7.

Example 4: Synthesis of Form K

Form K was obtained by dynamic vapor sorption of Form 2.

Polymorph Form K is characterized by the XRPD pattern provided in FIG. 9.

The DSC spectrum of Form K, provided in FIG. 10, shows two endotherms at 38.7° C. and 117.7.0° C. (onset temperature).

The TGA profile of Form K, provided in FIG. 10, shows a loss of about 1.9% of the weight of the sample as the temperature was increased to about 66° C.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

All of the patents, patent applications and publications referred to herein are incorporated herein in their entireties. Citation or identification of any reference in this application is not an admission that such reference is available as prior art to this disclosure. The full scope of the disclosure is better understood with reference to the appended claims.

What is claimed is:

1. A crystalline form of 2-methyl-1-[(4-[6-(trifluoromethyl) pyridin-2-yl]-6-{[2-(trifluoromethyl) pyridin-4-yl]amino}-1,3,5-triazin-2-yl)amino]propan-2-ol, wherein the crystalline form is characterized by an X-ray powder diffraction pattern presented in FIG. 1.

2. A crystalline form of 2-methyl-1-[(4-[6-(trifluoromethyl) pyridin-2-yl]-6-{[2-(trifluoromethyl) pyridin-4-yl]amino}-1,3,5-triazin-2-yl)amino]propan-2-ol, wherein the crystalline form is characterized by an X-ray powder diffraction pattern presented in FIG. 4.

3. A crystalline form of 2-methyl-1-[(4-[6-(trifluoromethyl) pyridin-2-yl]-6-{[2-(trifluoromethyl) pyridin-4-yl]amino}-1,3,5-triazin-2-yl)amino]propan-2-ol, wherein the crystalline form is characterized by an X-ray powder diffraction pattern having peaks at 2θ angles of 16.58, 18.49, and 24.32°±0.2° 2θ.

4. The crystalline form of claim 3, characterized by an X-ray powder diffraction pattern presented in FIG. 7.

5. A crystalline form of 2-methyl-1-[(4-[6-(trifluoromethyl) pyridin-2-yl]-6-{[2-(trifluoromethyl) pyridin-4-yl]amino}-1,3,5-triazin-2-yl)amino]propan-2-ol, wherein the crystalline form is characterized by an X-ray powder diffraction pattern having peaks at 2θ angles of 21.29 and 21.79°±0.2° 2θ.

6. The crystalline form of claim 5, characterized by an X-ray powder diffraction pattern presented in FIG. 9.

7. A pharmaceutical composition, comprising the crystalline form of claim 1, and a pharmaceutically acceptable excipient.

8. A method of treating or ameliorating one or more symptoms of a disease selected from the group consisting of a hematological malignancy and a solid tumor, each characterized by the presence of a mutant allele of IDH2, comprising administering to a subject having the disease a therapeutically effective amount of the crystalline form of claim 1.

9. The method of claim 8, wherein the disease is characterized by the presence of a mutant allele of IDH2 and the absence of a mutant allele of FLT3.

10. The method of claim 8, wherein the disease is characterized by the presence of a mutant allele of IDH2 and the absence of a mutant allele of NRAS.

11. The method of claim 8, wherein the disease is a hematological malignancy.

12. The method of claim 11, wherein the hematological malignancy is selected from the group consisting of acute myelogenous leukemia, myelodysplastic syndrome, chronic myelomonocytic leukemia, myeloid sarcoma, multiple myeloma, lymphoma, angioimmunoblastic T-cell lymphoma, blastic plasmacytoid dendritic cell neoplasm and myeloproliferative neoplasm, each characterized by the presence of a mutant allele of IDH2.

13. The method of claim 12, wherein the hematological malignancy is acute myelogenous leukemia.

14. The method of claim 12, wherein the hematological malignancy is myelodysplastic syndrome.

15. The method of claim 8, wherein the disease is characterized by the presence of a mutant allele of IDH2 and a mutant allele of at least one second gene, wherein the second gene is selected from the group consisting of ASXL1 and SRSF2.

16. The method of claim 15, wherein the disease is characterized by the presence of a mutant allele of IDH2 and the absence of a mutant allele of at least one other gene, wherein the other gene is selected from the group consisting of KRAS, TP53, SETBP1, U2AF1, TCF3, STAG2, NRAS, JAK2 and BRAF.

17. The method of claim 8, wherein the solid tumor is selected from the group consisting of glioma, melanoma, chondrosarcoma, and cholangiocarcinoma, each characterized by the presence of a mutant allele of IDH2.

18. The method of claim 8, wherein the disease is relapsed or refractory.

19. The method of claim 8, further comprising administering a second active agent.

20. The method of claim 8, wherein the subject is a pediatric patient.

21. A method of treating or ameliorating one or more symptoms of a disease selected from the group consisting of a hematological malignancy and a solid tumor, each characterized by the presence of a mutant allele of IDH2, comprising administering to a subject having the disease a therapeutically effective amount of the crystalline form of claim 2.

22. A method of treating or ameliorating one or more symptoms of a disease selected from the group consisting of a hematological malignancy and a solid tumor, each characterized by the presence of a mutant allele of IDH2, comprising administering to a subject having the disease a therapeutically effective amount of the crystalline form of claim 3.

23. A method of treating or ameliorating one or more symptoms of a disease selected from the group consisting of a hematological malignancy and a solid tumor, each characterized by the presence of a mutant allele of IDH2, comprising administering to a subject having the disease a therapeutically effective amount of the crystalline form of claim 5.

* * * * *